(12) United States Patent
Tobia et al.

(10) Patent No.: US 8,629,302 B2
(45) Date of Patent: Jan. 14, 2014

(54) METHODS FOR PREPARING HYPERICIN

(76) Inventors: Alfonso J. Tobia, Doylestown, PA (US); Bernard E. Cabana, Biglerville, PA (US); Venkata Vadlapatla, Paoli, PA (US); Ronald H. Connolly, Philadelphia, PA (US)

( * ) Notice: Subject to any disclaimer, the term of this patent is extended or adjusted under 35 U.S.C. 154(b) by 0 days.

(21) Appl. No.: 13/496,340

(22) PCT Filed: Sep. 15, 2010

(86) PCT No.: PCT/US2010/048937
§ 371 (c)(1),
(2), (4) Date: Jun. 4, 2012

(87) PCT Pub. No.: WO2011/034922
PCT Pub. Date: Mar. 24, 2011

(65) Prior Publication Data
US 2012/0245392 A1    Sep. 27, 2012

Related U.S. Application Data

(60) Provisional application No. 61/242,492, filed on Sep. 15, 2009.

(51) Int. Cl.
  *C07C 45/61* (2006.01)
  *C07C 45/81* (2006.01)
(52) U.S. Cl.
  USPC .......................................... 568/315; 568/324
(58) Field of Classification Search
  USPC .................................. 568/315, 324; 422/186
  See application file for complete search history.

(56) References Cited

U.S. PATENT DOCUMENTS 5,120,412 A    6/1992    Mazur et al.
6,001,882 A    12/1999   Fox et al.

FOREIGN PATENT DOCUMENTS

WO    WO 93/14197 A1    7/1993

OTHER PUBLICATIONS

Product Safety Data Sheet. TOCRIS Bioscience. VIMRxyn (Hypericin); http://www.tocris.com/dispprod.php?ItemID=35804; Jul. 24, 2013.*
International Search Report (PCT/ISA/210) issued on Dec. 29, 2010 for International Application No. PCT/US2010/048937.
Jun. 5, 2013 European Search Report issued in European Application No. 10817759.3.

* cited by examiner

*Primary Examiner* — Sikarl Witherspoon
(74) *Attorney, Agent, or Firm* — Buchanan Ingersoll & Rooney PC

(57) ABSTRACT

The present invention provides a method for making hypericin comprising the steps of converting a protohypericin to a protohypericin salt, and irradiating the protohypericin salt with visible light to form hypericin. The present invention also provides an apparatus comprising a transparent column having a top end and a bottom end, an inlet attached to the column at the top end to flow reactants into the column, a container attached to the column at the bottom end; and a visible light source positioned to cast light on to the column. The present invention further provides a method for making hypericin using said apparatus.

19 Claims, 2 Drawing Sheets

METHODS FOR PREPARING HYPERICIN

BACKGROUND OF THE INVENTION

Hypericin is a constituent of plants belonging to the genus *Hypericum*. It was isolated from this natural source in a chemically pure state by H. Brockmann et al. (Ann. 1942, 553, 1). Hypericin appears in nature accompanied by the chemically related compound pseudo-hypericin.

The isolation of hypericin from *Hypericum* plants is not practical on a larger scale, because it requires a lengthy procedure involving extraction with large volumes of solvents and cumbersome chromatographic separations on silica gel columns. The main difficulty in obtaining hypericin in a pure state from the plant material resides in its separation from the accompanying pseudohypericin. This necessitates the aforementioned chromatography with the elution of a large number of fractions, only a few of which contain the pure desired material. The yield of hypericin from the plants is very low, not more than 0.3%, based on the dry plant material.

U.S. Pat. No. 5,120,412 ('412 patent) to Mazur et al., which is incorporated herein by reference, discloses a process for synthesizing hypericin from emodin. The process involves first converting emodin to emodin anthrone which is then dimerized to form protohypericin. The protohypericin is then converted to hypericin by visible light irradiation. This process, however, produces low yield and purity of the final product.

Therefore, there remains a need for a process capable synthesizing hypericin in high yield and high purity.

SUMMARY OF THE INVENTION

An object of the present invention relates to a process for producing hypericin at high yield and high purity. This process involves first converting emodin to emodin anthrone, which is then dimerized to from protohypericin. The protohypericin is then converted to a salt, such as a sodium or potassium salt, of protohypericin. Visible light irradiation, preferably at about 400-700 nm, is then used to convert the protohypericin salt to hypericin. The crude hypericin produced has a purity of at least about 95%.

Another object of the present invention provides a photoreaction system for converting protohypericin to hypericin. The system rapidly effects the conversion at high yield and purity. Preferably, the hypericin exiting the photoreaction system (crude hypericin) is at least about 95% pure.

A further object of the present invention relates to a method for purifying hypericin. The method includes dissolving the crude hypericin in a solvent, preferably a polar solvent such as methanol, by heating, preferably to about 50-55° C. The insoluble solid is filtered and washed with methanol. This filtered solid product is then dried, preferably in vacuo at about 50-60° C., to obtain hypericin at greater than 98% pure. The filtrate is also cooled to precipitate hypericin. The precipitated hypericin is then filtered and washed, preferably with 30-40% hexane in ethyl acetate. The precipitate is also dried, preferably in vacuo at about 50-60° C. to obtain hyperic at greater than 98% pure. In this purification method, the hypericin is obtained from the insoluble fraction, as well as the by recrystallization from the solvent.

DETAILED DESCRIPTION OF THE PREFERRED EMBODIMENT

The process of the present invention contains one or more of the following steps: (1) converting of emodin to emodin anthrone; (2) dimerizing emodin enthrone to form protohypericin; (3) converting the protohypericin to a protohypericin salt; and (4) converting the protohypericin salt to hypericin.

(1) Converting Emodin to Emodin Anthrone

Figure 1:
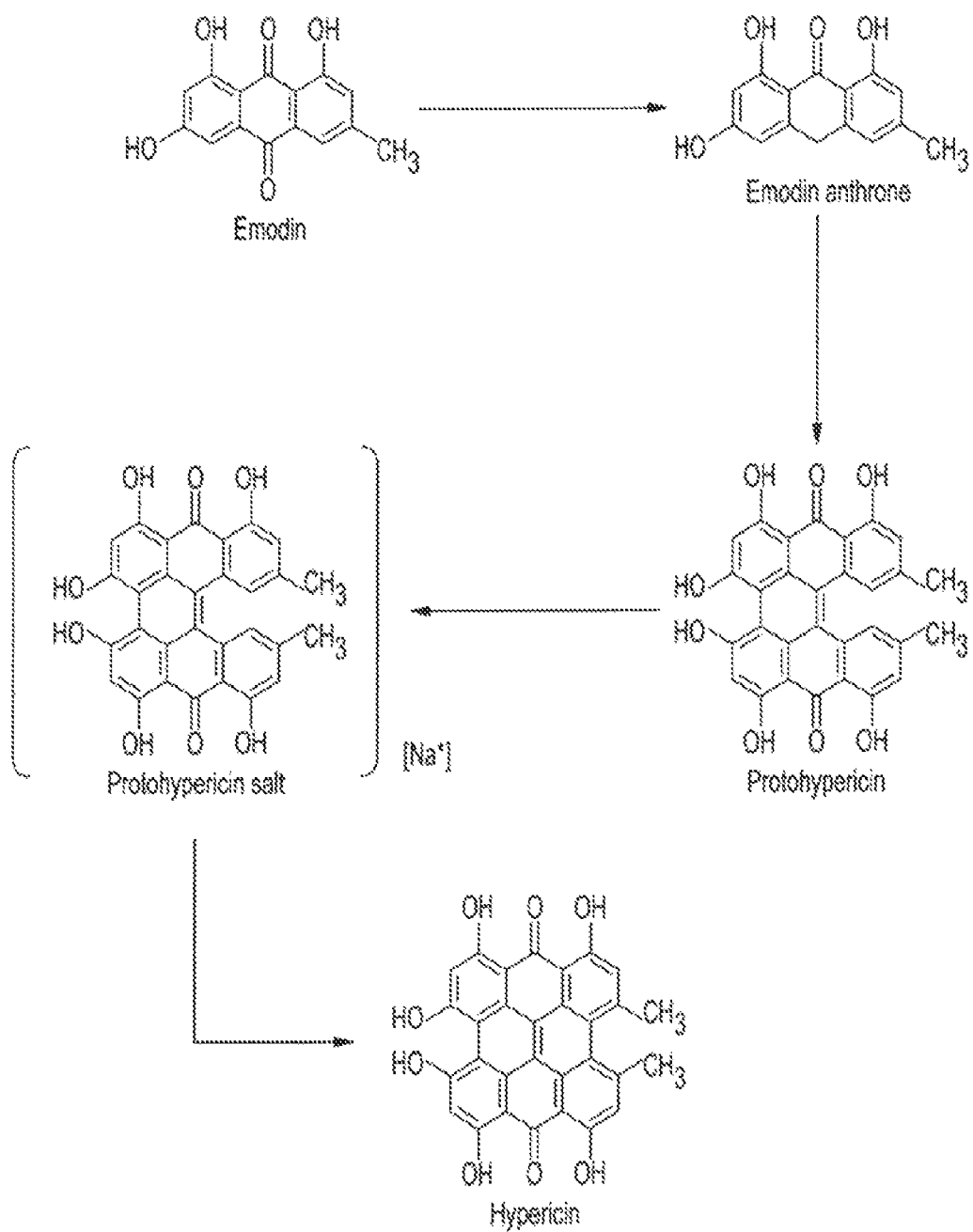
FIG. 1 shows the general reaction scheme for making protohypericin.

Emodin can be converted to emodin anthrone by the first reaction depicted in FIG. 1. In an embodiment, emodin is heated in the presence of a solvent, e.g. acetic acid, and a reducing agent, e.g. stannous chloride, preferably to reflux for about 1-4 hours by analytical monitoring of the reaction, e.g. by HPLC. The preferred solvent is a 2-5% acetic acid solution. In an embodiment, the ratio of emodin:acetic acid:stannous chloride in the reaction is 1 g:25-60 mL (2-5% solution):3.5-5.5 g. During the heating hydrochloric acid is slowly added to the mixture to maintain a highly acidic medium. Reflux is maintained for about one hour to two hours, preferably about one hour; after which, the mixture is cooled to room temperature. The emodin anthrone can then be filtered from the mixture and dried.

(2) Dimerizing Emodin Anthrone to Form Protohypericin

The protohypericin is formed by dimerization of emodin anthrone by reacting it with an oxygen transfer reagent in a solvent, preferably a tertiary aromatic amine, in the presence of a redox catalyst and a secondary amine. The emodin anthrone can be converted in high yield to protohypericin under selected specific conditions, namely, treating a solution of emodin anthrone in a tertiary amine solvent, preferably pyridine, containing a secondary amine, preferably piperidine, with a tertiary amine oxide, preferably pyridine N-oxide, in the presence of a conventional redox catalyst, preferably ferrous sulfate. This process is similar to that described in the '412.

Pyridine, pyridine N-oxide, ferrous sulfate, and emodin anthrone are heated, preferably to reflux and stirred. After about 2-3 hours, the reaction mixture is allowed to cool to about room temperature. The resulting dark color solution contains protohypericin. The solution can further be processed by filtering through celite (to remove insoluble solids/salts), concentrating (to remove pyridine solvent), and diluting in hydrochloric acid (remove residual pyridine by making HCl salt which will be washed out by water). This solution can then be dried to yield a dark powder containing protohypericin.

Although pyridine N-oxide is a preferred oxygen transfer reagent in the process according to the invention. However, other tertiary amine N-oxides (such as pyridazine N-oxide, pyrazine N-oxide, dimethylaniline N-oxide) or other oxygen transfer reagents, such as iodosobenzene, can be successfully used to convert emodin anthrone to protohypericin in high yield.

Among the conventional redox catalysts which are suitable for use in the process according to the invention, there may be mentioned divalent and trivalent nickel, iron and cobalt salts, especially sulfates or halides, e.g. chlorides. Among such salts, ferrous sulfate is a preferred catalyst. Alternatively, Group VIII metals, such as palladium or platinum on charcoal, can also be used as catalysts in this reaction.

Various tertiary aromatic amines can be used as solvents in the process of the present invention, pyridine being preferred.

Similarly, the secondary amine which must be present in the reaction mixture of the process according to the invention, can be selected from a wide variety of such compounds, piperidine being preferred.

(3) Converting the Protohypericin to a Protohypericin Salt

The protohypericin is converted to protohypericin salt by treatment with a base in an organic solvent. Preferably, the protohypericin is treated with sodium bicarbonate in acetone to produce protohypericin sodium. Although a sodium salt is preferred, other metal salts are also appropriate for the present invention, such as alkali metals and alkali earth metals. The preferred metals are potassium and sodium. Thus, in addition to sodium bicarbonate, other bases appropriate for the present invention, include, but are not limited to, sodium hydroxide and potassium hydroxide. Preferably, the weight ratio of sodium bicarbonate to protohypericin is about 2.8 to 3.3. This ratio produces about 1.7 to 2 mole equivalent of sodium for every mole of protohypericin. Thus, when other salts are used, this 1.7 to 2 (metal:protohypericin) molar ratio should be used.

Although acetone is the preferred solvent, other solvents can be used to covert protohypericin to protohypericin salt. Appropriate solvents can be, but are not limited to, acetone, ethyl acetate, and chloroform.

In an embodiment of the present invention, the solution of protohypericin and base in organic solvent is heated, preferably to about 40° C. to 50° C. This solution can also be filtered, e.g. through celite, to remove solid impurities.

It has been unexpectedly discovered that converting the protohypericin to a protohypericin salt prior allows for the next step in the process (converting of the protohypericin salt to hypericin) to produce purer product than the process disclosed in the '412 patent where the protohypericin is converted directly to hypercin.

(3) Converting the Protohypericin Salt to Hypericin

Figure 2:
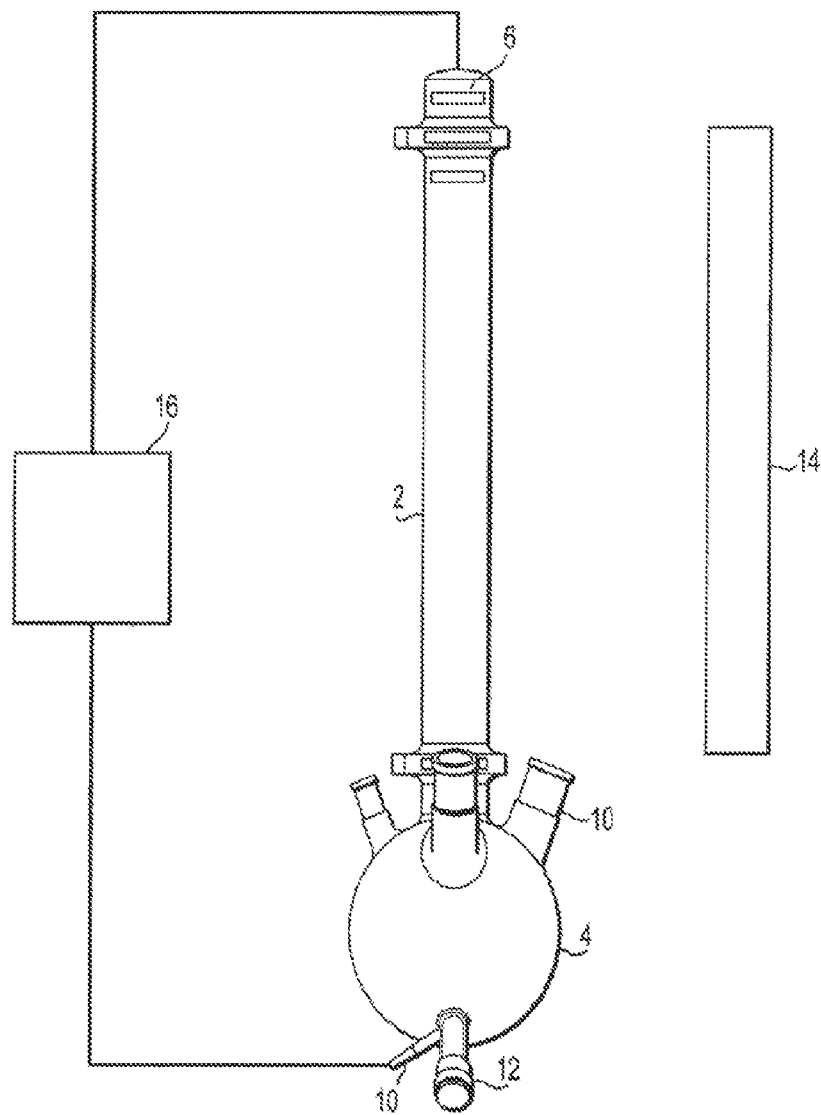
FIG. 2 is a drawing showing the reactor for the photoconversion of protohypericin (or protohypericin salt) to hypericin.

The protohypericin salt is converted to hypericin by irradiation with visible light. This process is disclosed in the '412 patent; however, that process results in low purity of the hypericin final product. The present invention provides an improved process and system for operating the photoreaction to improve yield and purity of the product, and to significantly shorten the process time. Referring to FIG. 2, the system of the present invention contains a transparent reaction column 2. At the bottom of the column 2 is a container 4 for collecting liquid flowing through the column 2. At the top of the column 2 is an inlet 6, preferably a shower nozzle, for flowing liquid into the column 2. The container 4 contains an opening to the atmosphere 8, a recycling port 10, and outlet port 12. The recycling port 10 is fluidly connected to a pump to pump the content of the container 4 to the inlet 6 at the top column 2 to recycle the liquid through the column 2. The outlet port 12 can be used to remove the hypericin product.

Surrounding the column 2 is at least one visible light source 14 directing light toward the column 2. The light preferably has wavelengths in the range of 400-700 nm, and placed about 5 to 12 inches from the column, more preferably about 5 inches.

In operation, the organic solution containing the protohypericin salt is pumped into the column 2 through the inlet 6. The inlet 6 flows to the solution into the column 2 in droplets, while, preferably, at the same time directing the droplets toward the wall of the column 2 to form a thin film of liquid flowing down the wall of the column. This flowing thin film is exposed to the light source 14, thus, converting the protohypericin salt in the thin film to hypericin. The liquid flowing through the column is then collected in the container 4 and recycled back to the top of the column 2, preferably via a pump 16. When the desired product conversion is reached, the photoreaction is terminated; and the product is removed from the system through the outlet port 12. The reaction is preferably monitored spectrophometrically. In this method, a sample is periodically removed from the reaction and the optical density (OD) of the sample is measured at 590 nm, 545 nm, and 330 nm. The reaction is terminated when the OD ratio at 590 nm to 545 nm ($OD_{590}/OD_{545}$) is greater than 1.8 and the OD ration at 590 nm to 330 nm ($OD_{590}/OD_{330}$) is greater than about 1.47. The photoreaction preferably takes place at about 15-30° C., more preferably at room temperature.

The column must be transparent so that the light can reach the protohypericin for the conversion to hypericin to occur. The column can be made of glass or polymer as long as it is transparent to the light.

Although the transparent column is disclosed above for the conversion of the protohypericin salt to hypericin, this same apparatus can also be used to convert protohypercin directly to hypericin.

Although the drawing generally depicts a cylindrical column, other column configurations can be used. For example, columns with star shaped or rectangularly shaped cross-section can be used to maximize the surface area of the column that is exposed to the light source. Column shapes and configurations that maximize surface area are preferred for the present invention.

The system of the present invention can also include mirrors, reflectors, lens, etc., to direct and/or focus light on to the column to maximize light exposure of the protohypericin or protohypericin salt flowing through the column.

The method and system of the present invention can be adapted for the synthesis of hypericin and hypericin derivatives alike. As used herein, the term "hypericin and hypericin derivative" means hypericin, protohypericin, pseudohypericin, helianthrone, or a combination thereof. It is clear to one of skill in the art that numerous insignificant modifications may be made to the chemical structure of hypericin, protohypericin, pseudohypericin, or helianthrone and that many such modifications will not significantly alter the biological activity of the molecule. Hence, hypericin, protohypericin, pseudohypericin, and helianthrone molecules which have been insignificantly modified, such that the biological activity is not significantly altered, are included within the definition of an appropriate hypericin derivative.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in these examples.

Example 1

Preparation of Emodin Anthrone

A mixture of 20 grams of emodin, 1000 mL of acetic acid, 82.8 grams of stannous chloride was heated to reflux. Hydrochloric acid (60 mL) was added slowly in minutes and continued reflux for 1 hour. Remaining 167 mL of HCl was added slowly at reflux and continued for an additional 1 hour. Orange color mixture was cooled to room temperature and left over night. Product was isolated by filtration and washed with water. Finally the product (emodin anthrone) was dried in vacuo at 60° C. to a constant weight to afford 18.1 grams (Yield: 95%) of an orange powder.

Example 2

Preparation of Protohypericin 350 mL of pyridine was heated to 60° C. and added 36.1 grams of pyridine N-oxide. 0.95 gram of ferrous sulfate and 18 grams of emodin anthrone were mixed and heated to reflux (180° C.). Piperidine (30.6 g) was charged to the mixture and the dark color solution was stirred for 3 hours at reflux. The mixture was allowed to cool to room temperature and left overnight. Dark color mixture was filtered through celite and concentrated under vacuum to approximately 40 mL volume. A mixture of 183 mL of concentrated HCl and 383 mL of water was added with stirring. The product was dried in vacuo at 60° C. to a constant weight to afford 18.8 grams (Yield 100%) of a dark powder containing protohypericin. Purity data is depicted in Table 1 (Batch No. 001-94).

Example 3

Preparation of Protohypericin Sodium

Protohypericin (18 g) was treated with sodium bicarbonate (5.6 g) in acetone (1.5 L) for 5 h at 45° C. The hot solution was filtered through celite and used to make crude hypericin.

Example 4

Preparation of Crude Hypericin

Acetone solution was charged into 5 L round bottom flask and pumped through the column (as described above) and re-circulated for 48 hours. The solution was exposed to two fluorescent lamps. The distance between the lamps and the column is approximately 6"-8". The reaction was monitored by UV spectrum. Solution samples were taken at 0, 24, and 50-hour time points. At each time point, the sample was dissolved in methanol and the UV-Visible spectrum was taken. The Optical Density (OD) ratios at 590 and 545 (ratio 1) and 590 and 330 nm (ratio 2) for each sample were determined. Reaction was stopped after the two ratios met the specification of 1.80 (ratio 1) and 1.47 (ratio 2) respectively.

After the reaction stoppage, the solvent was evaporated to reduce the volume to 30 mL. Hexane (50 mL) was added and stirred for 10 minutes. Product was isolated by filtration and washed the product with hexane. The product was dried in vacuo at 60° C. to a constant weight to afford 9 grams (Yield 50%) of a dark powder containing hypericin. Purity data is depicted in Table 1 (Batch No. 001-95).

Example 5

Purification of Hypericin

Crude hypericin was crystallized by dissolving 8.9 grams in 500 mL methanol and heated to 50° C. for 30 minutes. Insoluble solid was filtered and washed with 25 mL methanol. Solid product was dried in vacuo at 50° C. to a constant weight to afford 4.5 grams (Yield 50.6%) of a dark powder containing hypericin (Batch No. 001-96A).

The filtrate was cooled to 0° C.-5° C. and stirred for 5 hours and left in the refrigerator. Mixture was further cooled to −30° C. and stirred for 2 hours. The product was filtered, washed with cold Ethyl acetate:Hexane mixture (3:7). Finally the product was dried in vacuo at 50° C. to a constant weight to afford 1.5 grams (Yield 16.8%) of a dark powder containing hypericin (Batch No. 001-96B). See Table 1 for purity data.

TABLE 1

HPLC Purity Data

| Name | Batch No. | RRT (%) | | | | | | | | | |
|---|---|---|---|---|---|---|---|---|---|---|---|
| | | 0.44 | 0.61 | 0.65 | 0.79 | 0.82 | 1.00 | 1.83 | 1.88 | 1.96 | 2.00 |
| Protohypericin | 001-94 | | | | | 82.8 | 13.0 | | | | |
| Crude Hypericin | 001-95 | 0.13 | 0.52 | 0.22 | | 4.57 | 93.3 | 0.38 | 0.19 | 0.52 | — |
| Hypericin | 001-96A[1] | — | 0.27 | — | — | 2.05 | 95.8 | — | 0.60 | 0.36 | 0.82 |
| Hypericin | 001-96B[2] | — | 0.47 | — | | 0.68 | 98.8 | — | — | — | — |

[1]Isolated as insoluble portion from methanol in crystallization step (see Example 5)
[2]Isolated from methanol after crystallization (see Example 5)

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for making hypericin comprising the steps of:
   (a) converting a protohypericin to a protohypericin salt; and
   (b) irradiating the protohypericin salt with visible light to form hypericin.

2. The process of claim 1, wherein the protohypericin is formed by dimerizing emodin anthrone.

3. The method of claim 2, wherein the dimerizing step comprises reacting the emodin antrone with an oxygen transfer reagent in a tertiary aromatic amine solvent in the presence of a redox catalyst and a secondary amine.

4. The method of claim 3, wherein the oxygen transfer agent is oxygen transfer reagent is a tertiary amine oxide.

5. The method of claim 4, wherein the tertiary amine oxide is selected from the group consisting of pyridine N-oxide, pyridazine N-oxide, pyrazine N-oxide, and N,N-dimethylaniline N-oxide.

6. The method of claim 3, wherein the tertiary aromatic amine solvent is pyridine.

7. The method of claim 3, wherein the secondary amine is piperidine.

8. The method of claim 3, wherein the redox catalyst is selected from the group consisting of sulfate and halide salts of $Ni^{+2}$, $Ni^{+3}$, $Fe^{+2}$, $Fe^{+3}$, $Co^{+2}$ and $Co^{+3}$; and palladium and platinum metals on charcoal.

9. The method of claim 3, wherein the redox catalyst is ferrous sulfate.

10. The method of claim 1, wherein step (a) involves reacting protohypericin with a base.

11. The method of claim 1, wherein the base is a metal bicarbonate or a metal hydroxide.

12. The method of claim 11, wherein the base is selected from the group consisting of sodium bicarbonate, sodium hydroxide, calcium hydroxide, and potassium hydroxide.

13. The method of claim 11, wherein the metal is present at about two mole equivalent per mole of protohypericin.

14. The method of claim 1, wherein step (b) takes place in a transparent column.

15. A method for purifying hypericin comprising the steps of:
   (a) dissolving crude hypericin in a solvent to form a solution;
   (b) filtering the solution to produce a filtrate and a solid portion containing impure hypericin; and
   (c) recrystallizing hypericin from the filtrate.

16. The method of claim 15, wherein the solvent is methanol.

17. The method of claim 15, wherein step (c) comprises cooling the filtrate to about 0° C.-5° C. for about five hours and further cooling to about −30° C.

18. The method of claim 15, further comprising washing the precipitate.

19. The method of claim 18, wherein the precipitate is washed with a cold ethyl acetate/hexane mixture.

* * * * *